United States Patent
Portillo Rosado

(10) Patent No.: US 12,234,432 B2
(45) Date of Patent: Feb. 25, 2025

(54) NON-HYDROLYZED COLLAGEN-BASED MULTIUSE CLEANING COMPOSITION

(71) Applicant: Rosa Maria Portillo Rosado, Distrito Nacional (DO)

(72) Inventor: Rosa Maria Portillo Rosado, Distrito Nacional (DO)

( * ) Notice: Subject to any disclaimer, the term of this patent is extended or adjusted under 35 U.S.C. 154(b) by 607 days.

(21) Appl. No.: 17/621,277

(22) PCT Filed: Jun. 17, 2020

(86) PCT No.: PCT/DO2020/050001
§ 371 (c)(1),
(2) Date: Dec. 21, 2021

(87) PCT Pub. No.: WO2020/253929
PCT Pub. Date: Dec. 24, 2020

(65) Prior Publication Data
US 2022/0306967 A1  Sep. 29, 2022

(30) Foreign Application Priority Data

Jun. 21, 2019 (DO) ................. P2019-0173

(51) Int. Cl.
| | | |
|---|---|---|
| C11D 3/384 | (2006.01) | |
| C11D 1/26 | (2006.01) | |
| C11D 3/04 | (2006.01) | |
| C11D 3/20 | (2006.01) | |
| C11D 3/50 | (2006.01) | |

(52) U.S. Cl.
CPC ............. *C11D 3/384* (2013.01); *C11D 1/26* (2013.01); *C11D 3/046* (2013.01); *C11D 3/2003* (2013.01); *C11D 3/50* (2013.01)

(58) Field of Classification Search
CPC .. C11D 3/384; C11D 1/40; C11D 1/83; C11D 1/88; C11D 1/146; C11D 3/48; C11D 3/50; C11D 7/46; C11D 2111/14
See application file for complete search history.

(56) References Cited

U.S. PATENT DOCUMENTS

| | | | | |
|---|---|---|---|---|
| 3,991,184 | A * | 11/1976 | Kludas ................. | A61Q 19/00 514/801 |
| 2005/0226830 | A1* | 10/2005 | Fang ................... | A61K 36/537 424/769 |
| 2010/0330135 | A1* | 12/2010 | Tashiro ................. | A61Q 19/08 424/401 |
| 2010/0330214 | A1* | 12/2010 | Kim .................... | A61K 8/9789 424/773 |
| 2018/0369114 | A1* | 12/2018 | Kim .................... | A61K 8/64 |
| 2019/0307682 | A1* | 10/2019 | Angel .................. | A61K 31/4436 |

FOREIGN PATENT DOCUMENTS

| | | |
|---|---|---|
| CN | 104152285 A | 11/2014 |
| CN | 104263545 A | 1/2015 |
| CN | 104277927 A | 1/2015 |
| CN | 104277930 A | 1/2015 |
| CN | 104739747 A | 7/2015 |
| CN | 106318659 A | 1/2017 |
| CN | 106939212 A | 7/2017 |
| CN | 107661272 A | 2/2018 |
| JP | 0657626 A | 3/1994 |

OTHER PUBLICATIONS

European Patent Office, Communication pursuant to Art. 94(3) EPC issued by the European Patent Office on Mar. 22, 2024 in respect of the corresponding European patent application No. 20826196.6, Mar. 22, 2024, European Patent Office, Postbus 5818, 2280 HV Rijswijk, Netherlands.

"Essential oil", Internet Citation, Sep. 21, 2011 (Sep. 21, 2011), pp. 1-5, XP002675166, Retrieved from the Internet: URL:http://en.wikipedia.org/w/index.php?title=Essential_oil&oldid=451723320&printable=yes (Link as provided within above-referenced EPO Communication; "document D8".).

National Office of Industrial Property of the Dominican Republic; portions of Office Action in Applicant's possession; date unknown.

Oficina Espanola De Patentes Y Marcas, International Search Report for PCT/DO2020/050001, Jul. 22, 2020, Paseo de la Castellana, 75-28071 Madrid (Espana).

Oficina Espanola De Patentes Y Marcas, Written Opinion of the International Searching Authority (English Translation Thereof) for PCT/DO2020/050001, Jul. 22, 2020, Paseo de la Castellana, 75-28071 Madrid (Espana).

Ficina Espanola De Patentes Y Marcas, International Preliminary Report on Patentability for PCT/DO2020/050001, Sep. 2, 2021 (issue date) / Dec. 7, 2021 (translation date), Paseo de la Castellana, 75-28071 Madrid (Espana).

Annex to the International Preliminary Report on Patentability (Chapter II) for PCT/DO2020/050001 (English Translation); Sep. 13, 2021.

National Industrial Property Office, "Fund Requirement" (Office action), Jun. 3, 2020, National Industrial Property Office, Av. Los Proceres No. 11, Santo Domingo, Dominican Republic. (File name 1st_fund_requirement-orig.pdf).

English Translation of National Industrial Property Office, "Fund Requirement" (Office action), Jun. 3, 2020, National Industrial Property Office, Av. Los Proceres No. 11, Santo Domingo, Dominican Republic. (File name 1st_fund_requirement-ENG-TRANS.pdf).

(Continued)

*Primary Examiner* — Charles I Boyer

(57) ABSTRACT

The present invention relates to multi-use cleaning and degreasing detergent compositions, based on non-hydrolysed collagen, with improved cleaning and biodegradable properties, wherein the non-hydrolysed collagen is the surfactant and its presence in the composition, when formulated together with other surfactants, boosts the cleaning and degreasing effect of the composition as a result of the optimal quantitative ratio of the ingredients thereof and the synergy displayed between the non-hydrolysed collagen and the surfactant, and wherein the ranges by weight of the collagen and the surfactants do not exceed 25-30% by weight of the composition.

6 Claims, No Drawings

(56) References Cited

OTHER PUBLICATIONS

National Industrial Property Office, "Fund Requirement" (Office action), Nov. 12, 2020, National Industrial Property Office, Av. Los Proceres No. 11, Santo Domingo, Dominican Republic. (File name 2nd_fund_requirement-orig.pdf).

English Translation of National Industrial Property Office, "Fund Requirement" (Office action), Nov. 12, 2020, National Industrial Property Office, Av. Los Proceres No. 11, Santo Domingo, Dominican Republic. (File name 2nd_fund_requirement-ENG-TRANS.pdf).

National Industrial Property Office, "Resolution No. 171-2021", Mar. 18, 2021, National Industrial Property Office, Av. Los Proceres No. 11, Santo Domingo, Dominican Republic. (File name RESOLUTION_171-2021.pdf).

English Translation of National Industrial Property Office, "Resolution No. 171-2021", Mar. 18, 2021, National Industrial Property Office, Av. Los Proceres No. 11, Santo Domingo, Dominican Republic. (File name RESOLUTION_171-2021-ENGL-TRANS.pdf).

National Industrial Property Office, "Resolution No. 371-2021", Jun. 23, 2021, National Industrial Property Office, Av. Los Proceres No. 11, Santo Domingo, Dominican Republic. (File name RESOLUTION_371-2021.pdf).

English Translation of National Industrial Property Office, "Resolution No. 371-2021", Jun. 23, 2021, National Industrial Property Office, Av. Los Proceres No. 11, Santo Domingo, Dominican Republic. (File name RESOLUTION_371-2021-ENGL-TRANS.pdf).

Patent Office of State Intellectual Property Office, "First Review Notice of Observation", Issued Aug. 4, 2023, 7/F, Saite Plaza, No. 22 Jianwai Avenue, Chaoyang District, Beijing Beijing Jijia Intellectual Property Agency Co. Gao Shihao ((8610) 59208888) Huang Shui Na ((8610) 59208888).

Machine-Translated copy of item 1 immediately above.

* cited by examiner

NON-HYDROLYZED COLLAGEN-BASED MULTIUSE CLEANING COMPOSITION

FIELD OF THE INVENTION

The present invention relates to detergent and cleaning compositions. More particularly, it relates to a multiuse composition with cleaning and degreasing properties, wherein the non-hydrolysed collagen is the surfactant agent and its presence in the composition, when formulated alone or together with other surfactants, boosts the cleaning and degreasing effect of the composition as a result of the optimal quantitative ratio of the ingredients thereof and the synergy displayed between the non-hydrolysed collagen and the surfactant.

BACKGROUND OF THE INVENTION

Cleaning products sold on the market today cover various uses, fundamentally relating to personal hygiene and home cleaning. The use of these products is indispensable in daily life, not only because they generally contribute to cleaning, but because they furthermore play an important role in the prevention of diseases. Increasingly more recommendations and demands arise with respect to the qualities required of these products, mainly those related to the need to include improvements from the physicochemical, hygienic-sanitary and legal viewpoints. As for the aspect of improvements from a legal viewpoint, they often relate to usage restrictions on products declared toxic by international regulatory agencies, where the biggest challenge of this market is guaranteeing harmless, higher quality products to effectively meet the demands of consumers.

At present, the quality and efficacy rate demands by consumers of such products are very high. The raw materials that can be used, derived from the heightened requirements set forth by regulatory agencies having considerably increased the cost of these products, impacting the production process, the environment, and ultimately the price at which the products will finally be offered on the market.

There are several toxic ingredients acknowledged to be used in cleaning products which greatly affect health. For example, these types of products usually contain acids and abrasive products that are harmful when handled, particularly if there are children in the house, furthermore, their effects on surfaces to be cleaned are not always the desired effects.

Other ingredients commonly present in these cleaning products are highly toxic and present a high risk to health when inhaled or taken into the body by direct contact on the skin, an example of ingredients of this type in cleaning products are phthalates, which are used in products for the home such as fragrances, air fresheners, detergent, this ingredient could be in a given cleaning product, but the manufacturer is not required to declare it as an ingredient on the label because simply mentioning that it is an "artificial aroma or perfume" meets legal requirements; the reality is, however, that there are many phthalate-containing products on the market. This ingredient, known as an endocrine disruptor, has very serious effects on health, lowering sperm in men and possibly causing a number of conditions in women.

Another one of the ingredients commonly used in the composition of these products is triclosan, which is present in most detergents, dishwashing soap liquids and toilet soaps labelled as "antibacterial" it is an agent that is recognised as an aggressive antibacterial which can even promote the growth of drug-resistant bacteria and fight against those which are favourable and necessary for human existence. Furthermore, it builds up as the end of the consumption chain in rivers and streams and is harmful to the aquatic environment.

Quaternary ammonium ingredients are often found in fabric softeners and in most domestic cleaning products also labelled as "antibacterial". 2-Butoxyethanol, for example, is generally found in universal cleaning products but is primarily used as an ingredient in glass cleaning products. However, according to studies conducted by the EPA (US Environmental Protection Agency), it is reported that most cleaning products used in the home contain ingredients capable of harming ecosystems and even the health of human beings.

Today there are between 120,000 and 150,000 synthetic chemical substances coexisting with people on a daily basis, and although each of them has been studied individually, little is known of their "cocktail effect". For that reason, the paradigm of toxicology is changing and has already proven that exposure to very small doses prolonged over time is not only not good but can even be hazardous to human health. The EPA states that if these products are used in enclosed areas, they can cause a sore throat due to inhalation, contribute to narcosis, pulmonary oedema and cause serious liver and kidney damage.

Chlorine, for example, is also a very common ingredient in bleaches, abrasive powders, toilet cleaning products and mould removal products, however, it is officially reported that exposure to this hazardous element can cause chronic respiratory, kidney and digestive health problems, it is furthermore acknowledged to be a serious thyroid disruptor. Sodium hydroxide, also known as caustic soda, is another common ingredient in oven cleaning products and drain cleaning products, however, it is acknowledged for its high corrosive power to the point where if it comes into contact with the skin or eyes, it can cause serious burns and inhaling it can even cause an intense sore throat that may last for several days.

The aggressiveness demonstrated in many of the ingredients sold today on the market as cleaning products has brought about campaigns aimed at demanding heightened safety in homes and drastically changing the consumption habits related to such products.

Detergents called anionic detergents, for example, release a negative charge (anion) into an aqueous solution, the hydrophilic part thereof is negative charged and normally used because of its high foaming power. Among the most recognised anionic detergents are alkylbenzene sulphonate, alkyl ether sulphate, alkyl sulphate, sodium dodecyl sulphate as they are very effective detergents that are therefore used in clothes detergents and cleaning products. In the particular case of sodium dodecyl sulphate or sodium lauryl sulphate, it is made up of a chain of twelve carbon atoms linked to a sulphate group, conferring to the molecule the amphiphilic properties required of a detergent. It is regarded as the most widely used surfactant in cleaning products, toothpaste, shampoos, shaving foams, and bubble baths.

In turn, organic acid esters of plant origin are used in detergents as a thickening, foam stabilising and degreasing agent that largely reduces the requirements for salt to thicken formulations such as shampoos today without salt used for washing hair that has been subject to aggressive treatments, such as keratins for straightening. An example of these esters is coconut oil diethanolamide commonly sold at 60%, sold under recognised brands such as Amizur 60 or Cocamide MEA. This ingredient is hard to dissolve in water; however, in mixtures with soap and other surfactants, it can become a transparent solution which achieves perfect foam stabilisation, suitable thickening, moisturising, tolerance to hard water and highly biodegradable. One of the fundamental applications of collagen is the cosmetics industry given its recognised skin and hair protective action, giving them more vitality. Collagen is used as an ingredient in antiwrinkle creams, face masks, toners and conditioners. Furthermore, collagen is an ingredient used in the preparation of some liquid detergents, in the form of collagen hydrolysate (CH), and the known use of this product up until now is mentioned or described exclusively as a nutraceutical and protective agent for the skin of users, but it is not known for its surfactant and degreasing properties.

In the state of the art, several detergent formulations are known and some of them constitute patented compositions using these ingredients mentioned above.

Patent CN1153206, LIN YIFEI et al., proposes a multi-functional detergent composition for washing one's hair, clothes and tableware which contains in its composition 6-8% sodium silicate; said composition presents whitening action, and further comprises coconut oil, fatty acid, diethanolamine at 5-7%, carboxymethylcellulose sodium at 0.8-1%, ethylenediaminetetraacetic acid (EDTA) at 0.8-2.5% and citric acid: 0.8-0.5%.

Another similar liquid composition for washing dishes is proposed in patent CN106398891 defining proportions in parts, that is, 10 to 22 parts of maleic rosin-polyoxyethylene octylphenol ether diester sodium carboxylate, 5 to 9 parts of collagen, 4 to 9 parts of tartaric acid, 2 to 5 parts of trimethylglycine, 12 to 15 parts of ginger powder, 4 to 8 parts of coconut fatty acid diethanolamide, 7 to 16 parts of ammonium laureth sulphate, 2 to 9 parts of polyoxyethylene fatty sodium alcohol sulphate, 9 to 20 parts of chamomile extract, 11 to 30 parts of *euphorbiae* hirtae extract, 28 to 45 parts of fructus gleditsiae extract, 15 to 25 parts of ethylene glycol, 5 to 10 parts of lauryl alcohol, 8 to 16 parts of glycerol, 10 to 14 parts of coconut diethanolamide, 3 to 7 parts of cucumber vine powder, 3 to 5 parts of garlic powder, 4 to 9 parts of melilotus *albus,* 3 to 7 parts of cinnamon essential oil, 10 to 25 parts of polyoxyethylene lauryl ether sodium sulphate, 3 to 5 parts of table salt. The sole objective of this product is to be an easy-to-use dishwashing product with a good foaming effect, assuring a reduction in the water volume used in the dishwashing process and reducing the undesirable residual odour.

ZHU JIACHENG et al. propose in patent CN106318659 a detergent composition that guarantees hand care, prepared with an ingredient ratio by weight of 4-7 parts of glycerine, 10-15 parts of fatty alcohol-polyoxyethylene ether sodium sulphate, 8-12 parts of dodecyl benzene sodium sulphonate, 2-5 parts of trisodium citrate, 9-13 parts of tea tree essential oil, 1-3 parts of essence, 3-6 parts of cucumber extract, 2-6 parts of collagen, 0.5-1.5 parts of sodium oxide and a suitable amount of water. This detergent composition is considered to guarantee hydrating effects and does not cause skin irritation or dryness, even for people with sensitive skin.

Patent CN104277927 by LI PENG et al. proposes a detergent composition for daily use, wherein said composition is enriched with multiple amino acids of arginine to ensure care for clothing, comprising an ingredient ratio in percentage by weight of 10-15.0% of fatty alcohol polyethenoxy ether sodium sulphate, 8-15% of collagen, 2.0-8.0% of sodium dodecyl sarcosine, 0.1-0.5% of isoleucine, 1-2% of aromatic amino acid, 1-2% of heterocyclic amino acid, 0.2-0.4% of leucine, 0.2-0.4% of threonine, 0.1-0.5% of methionine, 0.2-0.4% of cysteine, 0.5-3% of coconut oil alcohol amide, 0.05-0.5% of essence, 0.1-1% of sodium chloride, 0.2-0.4% of preservative and deionised water.

Patent CN104152285 by XUN WENJIE et al. shows a neutral liquid detergent for daily use, the components of which in percentage by weight are: 10 to 15.0% of sodium alcohol sodium sulphate, 5 to 12% of soybean collagen, 2.0 to 8.0% of sodium dodecyl sarcosinate, 0.2 to 0.4% of amino acid moisturising agent, 0.1 to 0.5% of vitamin E, 0.5 to 3% of coconut oil alcohol amide, 0.05 to 0.5% of essence, 0.1 to 1% of sodium chloride, 3 to 6% of citric acid, 1 to 3% of caustic soda flakes, 0.2 to 0.4% of antiseptic, and the rest is deionised water.

Patent CN102453634 proposes another liquid detergent composition for dishes which does not affect the skin on the hands; in this case the proposed composition is made up of 2-5% of glycerol, 1-2% of glyceryl stearate, 3-5% of collagen, 8-10% of fatty alcohol polyethenoxy ether sodium sulphate, 0.2-0.5% of sodium tetraborate, 0.03-0.05% of chlorine dioxide, 0.1-0.2% of solid caustic soda, 0.3-0.7% of alkylolamide, 0.1-0.5% of alkyl glucoside, 0.02-0.05% of alkyl betaine, 0.2-0.3% of solubiliser, 0.05-0.1% of essence, 0.02-0.05% of pigment, 0.02-0.05% of preservative and the rest deionised water.

Patent CN106939186 describes a similar detergent, with the particularity that it does not affect the skin on the hands, wherein the mentioned composition contains 4-7 parts of glycerine, 10-15 parts of fatty alcohol polyoxyethylene ether sulphate, 8-12 parts of dodecylbenzene sodium sulphonate, 2-5 parts of trisodium citrate, 9-13 parts of tea tree essential oil, 1-3 parts of essences, 3-6 parts of cucumber extract, 2-6 parts of collagen, 0.5-1.5 parts of sodium oxide, a suitable amount of water.

Patent CN104263545 by GUAN L I et al. proposes another composition of a non-irritating washing-up liquid from the following components in percentage by weight: 5-10% of sodium lauryl sulphate, 5-10% of laurinol polyoxyethylene, 0.2-0.4% of amino acid moisturising agent, 1-3% of cucumber extract, 2-5% of cocamidopropyl betaine, 2-4% of collagen, 0.2-0.8% of vitamin E, 0.5-3% of cocamidopropyl dimethylamine oxide, 0.05-0.5% of essence and the rest deionised water.

TANAKA HIROMICHI et al. propose in patent JPH01204998 a detergent composition which scarcely irritates the skin and improves safety and detergency, the composition contains 0.01% by weight or more of collagen hydrolysate comprising a polypeptide having an average molecular weight adjusted to 1,000-7,000 or an oligopeptide having an average molecular weight adjusted to 500-1,000 is mixed with 0.1-50% by weight of an anionic, cationic, amphoteric or nonionic surfactant and optional additives such as builders, chelating agents, solvents, abrasives, pH adjusters, thickeners, hydrotropes, disinfectants, antiseptics, pigments, and perfumes.

Patent application WO9706780 by TOTANI NAGAO et al. relates to cosmetic preparations which guarantee a supply of creamy cosmetic agents, with stable foam while washing the hair and skin, in this case, the composition contains acyl lactylates, protein hydrolysates, fatty acid protein condensates, pointing out that the protein hydrolysates and collagen are preferably from soybean, almonds or rice wheat proteins and are at a proportion of 2 to 10%.

German patent DE3413475 by BERGERHAUSEN HEINRICH teaches a detergent composition for the skin generally used in these products in the form of washing lotions based fundamentally on liquid polyfluoroalkylidene, with a high action of removing grease from the skin, causing an unpleasant feeling in the skin due to the reaction with the surfactant agents, to avoid these unpleasant consequences, substances are incorporated for returning grease to the skin, adding polysaccharides to the composition, in particular N-guar-hydroxypropyltrimethylammonium chloride, together with a sodium alkyl sulphate-collagen complex as additive.

Lastly, patent CA1224211 by EIGEN EDWARD et al. proposes a liquid detergent composition which is substantially non-irritant comprising an aqueous solvent containing 10% to 50% by weight of a water-soluble anionic surfactant and about 0.2-5% by weight of a partially hydrolysed protein fraction.

As can be observed in these proposed detergent formulations available in the state of the art, the proportions of active ingredients, collagen, coco-diethanolamine and sodium lauryl sulphate, are fundamentally in a percentage-wise proportion, the ranges of which vary, for example, in the case of collagen, ranges vary between 0.25 and 12%, more specifically between 0.25 and 5%; the ingredient coco-diethanolamine is generally in a range which varies between 0.5 and 10%, and more commonly the proportions of this ingredient in these detergent formulations vary between 0.5 and 7%. In the case of the surfactant ingredient, sodium lauryl sulphate, the concentration ranges in these detergent solutions mostly vary between 10 and 50% and are preferably in lower ranges between 10 and 25%. They are all always combined with other ingredients to guarantee detergent power and foam stability and to minimise the aggressive effect on the skin on the hands.

However, these detergent formulations described above have the main drawback of requiring large amounts by weight in the formulation of surfactant and foaming substances in order to reduce surface tension on the surface to be cleaned, which helps to release dirt, rust and grime, generating undesired environmental impacts. These formulations mainly incorporate hydrolysed collagen in small amounts and as a protective agent for the skin of the users, but not non-hydrolysed collagen, which does not allow taking advantage of the surfactant and degreasing power of non-hydrolysed collagen, whether alone, in small amounts or associated with small amounts of surfactants, due to a surprising and unexpected feature that non-hydrolysed collagen presents when incorporated either alone or in minimum amounts, which is that it allows obtaining a multiuse cleaning product with improved biodegradable cleaning and degreasing properties.

DESCRIPTION OF THE INVENTION

Accordingly, an object of the invention relates to a multiuse cleaning and degreasing solution based on non-hydrolysed collagen, which allows an effective cleaning on metallic surfaces, the removal of any type of greases and various types of dirt, with a rapid effect and not aggressive for the skin and containing ingredients having a low environmental impact.

Another object of the present invention relates to a multiuse cleaning and degreasing solution, the improved cleaning effect of which corresponds to an optimal quantitative ratio of the fundamental active ingredients thereof, namely, non-hydrolysed collagen, surfactant and preservative.

Another object of the present invention relates to a cleaning solution, the cleaning and degreasing effect of which corresponds to an optimal quantitative ratio which allows non-hydrolysed collagen to release its surfactant, cleaning and degreasing effect.

Moreover, one object of the present invention relates to a multiuse cleaning and degreasing solution, the cleaning effect of which is boosted and is the direct result of the synergy of the non-hydrolysed collagen present in the formulation and the surfactant substances comprised in the cleaning solution, requiring smaller amounts of surfactants to achieve an improved degreasing, cleaning and foaming effect.

DETAILED DESCRIPTION OF THE INVENTION

As a results of the works done to improve these cleaning and degreasing detergent compositions, it has surprisingly been found that non-hydrolysed collagen, in addition to being an effective protecting agent of the skin and hair, when used without being hydrolysed it triggers an important cleaning and degreasing surfactant reaction, allowing multiuse organic and biodegradable cleaning compositions to be formulated alone, with a high cleaning and degreasing power, without the need to incorporate conventional surfactant compounds to said formulations or compositions, so non-hydrolysed collagen can be used as a substitute for conventional surfactants.

Moreover, it has surprisingly been found that when non-hydrolysed collagen is used, it allows the required amounts of conventional surfactants to be reduced, allowing multiuse cleaning formulations to be obtained with a high cleaning and degreasing power derived from the synergistic action of non-hydrolysed collagen which boosts the cleaning and degreasing effect of the surfactant substances present in the composition.

In both cases, whether the non-hydrolysed collagen is used as the only cleaning substance present in the composition or as a synergistic booster of conventional surfactant substances, the cleaning capacity and effective removal of a wide range of dirt, without generating skin conditions and improving the biodegradable properties of said cleaning compositions, increases considerably.

The following examples will allow for illustrating alternative multiuse biodegradable cleaning compositions, assuring that all the concentrations of the non-hydrolysed collagen and surfactants that are proposed are within the expressed percentage ranges and do not exceed 25%-30% of the total composition.

The surprising effect of the degreasing and cleaning detergent power is achieved by including in the composition the indicated amounts by weight of non-hydrolysed collagen when it acts as the only surfactant and degreasing element in the composition, or of non-hydrolysed collagen when it acts together with other surfactant substances, all expressed in the indicated percentage ranges and not exceeding 25%-30% of the total composition, and wherein the surfactant is selected from sodium lauryl sulphate, the thickening and foam stabilising substance conferring the desired viscosity of the product is preferably selected from Cocodiethanolamine or Comperlan; and a preservative preferably selected from DANTOGARD, methylchloroisothiazolinone and methylisothiazolinone, sodium benzoate, sodium sorbate or benzyl alcohol. Optionally, the composition may contain a natural fragrance selected from lemon, orange, apple, green tea, lavender, aloe vera, peach, among others. It has been found that with the use of this composition, there are no adverse effects on the skin, even with continued and systematic use, the cleaning process is efficient, and the composition entrains all the impurities rather effortlessly.

More particularly, the composition may contain the following proportion of components:

| | |
|---|---|
| Non-hydrolysed collagen | 1 to 30% |
| Preservative | 0.25 to 2% |
| Natural fragrances | 0.1 to 2% |
| Deionised water | 69 to 80%. |

More particularly, the composition may contain the following proportion of components.

| | |
|---|---|
| Non-hydrolysed collagen | from 1 to 30% |
| Cocodiethanolamine | 0.25 to 5% |
| Sodium lauryl sulphate | 1 to 17% |
| Preservative | 0.25 to 0.6% |
| Natural fragrances | 0.1 to 0.5% |
| Deionised water | 69 to 80% |

Likewise, the composition object of the present invention may also contain the following proportion of components:

| | |
|---|---|
| Non-hydrolysed collagen | 1 to 27% |
| Thickener and stabiliser | 0.25 to 5% |
| Surfactant | 1 to 5% |
| Preservative | 0.25 to 2% |
| Natural fragrances | 0.1 to 0.5% |
| Deionised water | 66 to 70%. |

Particular formulations that can be obtained from combining the components set forth above as particular exemplary embodiments given by way of illustration are set forth below.

Example 1

| | |
|---|---|
| Non-hydrolysed collagen | 30% |
| DANTOGARD preservative | 2% |
| Natural lemon fragrances | 2% |
| Deionised water | 66% |

This formulation was used for cleaning metallic surfaces, for example ovens and cooktops. It is applied on the surface and left to act for a time span of 2-5 minutes and it is then removed with a dry cloth, leaving the surface clean and with a protective covering that keeps the surface clean for a longer time.

Example 2

A composition containing the following ingredient ratio is prepared, wherein the preparation thereof is simple, simply mixing the ingredients at room temperature and stirring until a homogeneous solution is obtained:

| | |
|---|---|
| Non-hydrolysed collagen | 10% |
| Cocodiethanolamine | 3% |
| Sodium lauryl sulphate | 5% |
| Sodium sorbate preservative | 0.5% |
| Natural lavender fragrances | 1.5% |
| Deionised water | 80%. |

The composition was applied in a vehicle engine to remove grease, achieving an absolute cleaning effect; the product was applied, left to act for a time span of 2-5 minutes and removed with water.

Example 3

A composition containing the following ingredient ratio is prepared:

| | |
|---|---|
| Non-hydrolysed collagen | 1% |
| Comperlan | 2% |
| Sodium lauryl sulphate | 4% |
| DANTOGARD Preservative | 1.5% |
| Natural orange fragrances | 1.5% |
| Deionised water | 90% |

This formulation was used as a dishwashing soap, demonstrating that the product has excellent properties for this purpose, presents a good capacity to remove residues, very good viscosity, and does not cause unpleasant effects on the skin. Therefore, protective gloves are not required for systematic use.

Example 4

The proportion of ingredients used in this case was the following and the preparation process consisted of mixing the ingredients under normal stirring for a time span of 2 minutes until complete dissolution of the ingredients, the ratio of which in this case was:

| | |
|---|---|
| Non-hydrolysed collagen | 7% |
| Cocodiethanolamine | 1.5% |
| Sodium lauryl sulphate | 3% |
| Sodium sorbate | 2% |
| Natural green apple fragrances | 1.5% |
| Deionised water | 85% |

This formulation was used for cleaning metallic surfaces in work establishment furniture, such as in hair salons, wherein the action of certain typical hair care products, as well as hair clippings, contribute to an unpleasant image of the surface of the furniture. This same formulation was used to clean the metallic parts in bathrooms, such as fittings, where dirt residues together with the body grease and soap foam are often deposited, creating a layer of dirt. This formulation was applied gently with the help of a cotton or wool cloth. It was left to act for a time span of 2-5 minutes and did not require any effort in removing the dirt by mechanical entrainment, simply passing the cloth with the formulation over same and then removing it with the help of a dry cloth, which guarantees that the shine on all surfaces will be recovered.

Example 5

The proportion of ingredients used in this case was the following and the preparation process consisted of mixing the ingredients under normal stirring for a time span of 2 minutes until complete dissolution of the ingredients, the ratio of which in this case was:

| | |
|---|---|
| Non-hydrolysed collagen | 15% |
| Comperlan | 1% |

-continued

| | |
|---|---|
| Sodium lauryl sulphate | 2% |
| Sodium sorbate | 1% |
| Natural green apple fragrances | 1.5% |
| Deionised water | 79.5% |

This formulation was used as a shampoo for cleaning hair and the body. It was applied in a conventional manner, left to act for a time span of 2-5 minutes, and removed with abundant water, showing positive results and leaving silky, shiny hair and body.

Collagen has always been used in cleaning formulations as a moisturiser and protective agent for the skin, never by itself as a cleaning agent or surfactant. When collagen is not hydrolysed, it becomes a surfactant, presents degreasing and cleaning power, is capable of dissolving any type of dirt and grease without any effort in minimal time and without needing to use protective gloves.

The non-hydrolysed collagen formula used, only as a surfactant, with a preservative and a fragrance is used to wash a vehicle engine, it is applied with a sponge, left for 2 minutes and rinsed with water, leaving it without a drop of grease, shiny and without the need to use gloves, on the contrary, hands are moisturised and soft because it does not lose its moisturising power.

This same formula is applied in the kitchen of a restaurant that serves meat, on the grills and fume hoods, which have been covered for some time with grease and grime, leaving the stainless steel with many stains, it is sprayed on, simply wiped with a sponge (stainless steel cleaners are known to be highly toxic; in fact, their use is recommended in ventilated locations and wearing gloves), leaving the steel like new, with no grease or stains, and leaving a pleasant fragrance, without the need to wear gloves.

This same formulation used to wash a car engine and to clean grease in a restaurant is used to bathe a baby, leaving the skin clean, moisturised and very soft, and at the same time, the same formula is used to wash a woman's hair, which is left completely clean, shiny and silky.

At present, there is no formulation with these features which can be used to bathe a baby, wash hair, remove the grease in a car or clean the stainless steel in a kitchen without any effort, and while cleaning, rejuvenating and protecting skin, since non-hydrolysed collagen maintains its moisturising and rejuvenating properties, so gloves are not needed for this action.

This formula of non-hydrolysed collagen, the preservative and the fragrance is used. Added to it are a surfactant, in this case lauryl sulphate, a thickener and foam stabiliser, Comperlan, and deionised water to see how said surfactant was boosted in the presence of non-hydrolysed collagen and synergy is displayed because both of them are surfactants, but lauryl sulphate is aggressive as it breaks down oils and greases, and poorly treats, dries and flakes the skin. However, as a surfactant, as non-hydrolysed collagen breaks down grease, it does not lose its moisturising and protective properties of the skin, so they complement one another and synergy between them occurs. This allows the amount of surfactant with the presence of non-hydrolysed collagen to be reduced, where it can be reduced to a minimum amount, also resulting in a contribution to the environment since it is biodegradable, without losing cleaning properties but rather, on the contrary, boosting them.

The invention claimed is:

1. A multiuse cleaning degreasing composition comprising:
   A) between 1% and 30% by weight non-hydrolyzed collagen;
   B) between 0.25% and 2% by weight preservative substance;
   C) between 0.1% and 2% by weight natural fragrance;
   D) between 0.25% and 5% by weight cocodiethanolamine; and
   E) between 69% and 80% by weight deionized water, wherein the non-hydrolyzed collagen acts as a surfactant agent.

2. The composition of claim 1, wherein the preservative substance is selected from the group consisting of: DANTOGARD, methylchloroisothiazolinone, methylisothiazolinone, sodium sorbate, sodium benzoate and benzyl alcohol.

3. The composition of claim 1, wherein the natural fragrance is selected from the group consisting of: lemon, orange, apple, green tea, lavender, aloe vera and peach.

4. The composition of claim 1, wherein:
   said non-hydrolyzed collagen is present in an amount between 1% and 27% by weight;
   said natural fragrance is present between 0.1% and 0.5% by weight;
   said deionized water is present between 66% and 70% by weight; and
   wherein the composition further comprises between 1 and 5% by weight of an additional surfactant.

5. The composition of claim 4, wherein the additional surfactant is sodium lauryl sulphate.

6. A multiuse cleaning degreasing composition, based on non-hydrolyzed collagen, wherein the non-hydrolyzed collagen acts as a surfactant agent, and comprises by weight of the composition:
   A) between 1% and 30% non-hydrolyzed collagen;
   B) between 0.25% and 2% preservative substance selected from the group consisting of DANTOGARD, methylchloroisothiazolinone, sodium sorbate, or benzyl alcohol;
   C) between 0.1% and 2% natural fragrance;
   D) between 0.25% and 5% cocodiethanolamine as a thickening and foam stabilizing substance; and
   E) between 69% and 80% deionized water.

* * * * *